United States Patent [19]

Wojciechowicz, Jr.

[11] 4,442,840
[45] Apr. 17, 1984

[54] ELECTRICAL CONNECTOR APPARATUS AND METHOD FOR A TEMPORARY CARDIAC PACING WIRE

[76] Inventor: Alexander Wojciechowicz, Jr., 7 Herrontown Rd., Princeton, N.J. 08540

[21] Appl. No.: 385,931

[22] Filed: Jun. 7, 1982

[51] Int. Cl.³ .............................................. A61N 1/04
[52] U.S. Cl. .................................................. 128/419 P
[58] Field of Search ............... 339/139, 209; 128/419, 128/421–422, 639, 695–696

[56] References Cited

U.S. PATENT DOCUMENTS

| | | | |
|---|---|---|---|
| 3,918,440 | 11/1975 | Kraus | 128/419 F |
| 4,010,756 | 3/1977 | DuMont et al. | 128/419 P |
| 4,144,889 | 3/1979 | Tyers et al. | 128/419 P |
| 4,289,144 | 9/1981 | Gilman | 128/419 P |

FOREIGN PATENT DOCUMENTS 2157529  5/1973  Fed. Rep. of Germany ...... 128/335

OTHER PUBLICATIONS

Deal et al. "Temporary connecting lead for transvenous pacemakers" J. of Thoracic & Cardiovascular Surgery" vol. 55, No. 3, Mar. '68, pp. 359-360.

*Primary Examiner*—William E. Kamm
*Assistant Examiner*—Mitchell J. Shein
*Attorney, Agent, or Firm*—Richard C. Woodbridge

[57] ABSTRACT

An electrical connector for a temporary cardiac pacing wire is formed by placing a male lead through a connector body and securing it in place by means of a lockable cap. The male lead is formed by cutting or breaking the shaft of a Keith-type straight needle which is electrically connected to the center lead of the pacing wire. The lead with electrode wire attached thereto is passed through a resilient gasket and through an aperture in the connector body. The lockable cap is then locked onto the connector body so that the lead is sealed and cannot back out of the aperture. A pair of resilient spring-loaded arms connected to the cap carry a pair of opposed locking tabs. The locking tabs engage with corresponding locking detents in the connector body. The assembled connector can then be electrically connected in a conventional manner to medical instrumentation by plugging it into a corresponding extension cord set having mating female receptacles that mate with and seal against the body of the male connector. It is virtually impossible to pull the locking cap off of the connector body by accident once the connector is assembled.

10 Claims, 11 Drawing Figures

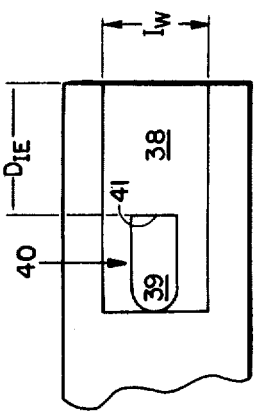
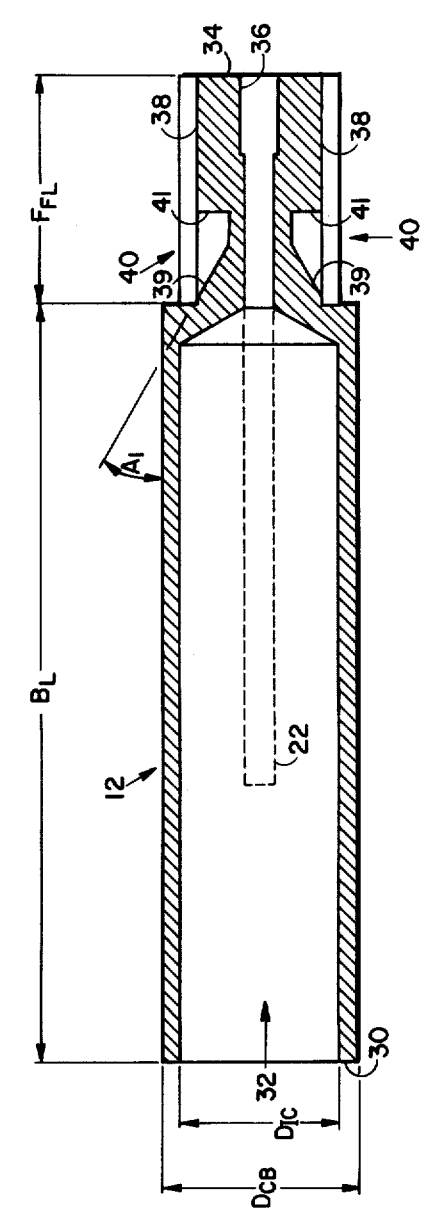
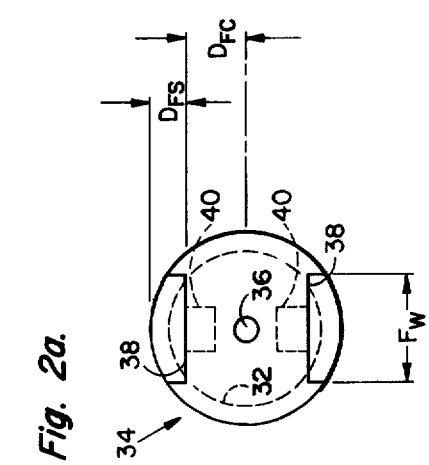

ELECTRICAL CONNECTOR APPARATUS AND METHOD FOR A TEMPORARY CARDIAC PACING WIRE

BACKGROUND OF THE INVENTION

1. Field of the Invention

This invention relates to an electrical connector of the sort used with temporary cardiac pacing wires.

2. Description of the Prior Art

A typical temporary cardiac pacing wire normally has the following elements: a sharp Keith-type straight cutting needle; a relatively soft multi-strand surgical steel wire having a soft plastic coating therearound; and a circular taper point needle. Both needles are swaged or otherwise connected directly onto the conducting steel wire. Wires of this sort are manufactured by the A & E Medical Division of the Alto Development Corporation of Farmingdale, N.J. The Model M-26 is one example. Another example is described in U.S. Pat. No. 4,010,756. The Keith-type straight needle described in that patent includes a weakened zone therein so that it may be snapped apart. The remaining shank portion is then used as a male lead for an electrical connector. The same result can be achieved by cutting the shank of a conventional Keith-type needle with a pair of diagonal pliers. The lead thus formed is attached to a therapeutic or diagnostic medical instrument by use of alligator clip leads or by plugging the lead directly into the hole and locking thumbscrew connections common to a great many pacemaker designs. These widespread methods of connecting the temporary pacing wires to the instrumentation leaves a lot to be desired because the connections are not electrically insulated or protected from contaminants; and they do not provide for protection of the lead when it is not in use. Connectors like the ones described above are in use today on a very limited basis. Most are custom-built and none use the lead formed from the shank of a Keith-type needle. Instead the Keith-type needle is completely cut off and the center conducting wire is exposed by stripping the insulation. The most common connector is believed to be manufactured by the AMP Corporation. That connector is described on pages 16 and 17 of a book entitled "Diagnosis and Treatment of Cardiac Arrhythmias Following Open Heart Surgery" published in 1980 by The Futura Publishing Company, Inc. of Mount Kiscoe, N.Y. The authors are Albert L. Waldo, M.D. and William A.H. MacLean, M.D. According to that disclosure the Keith-type straight needle is cut off completely after the wire electrode has been passed through the anterior chest wall of the patient. A small black rubber sealing grommet is placed on the wire then after stripping the wire a gold pin is attached to the wire using a special crimping tool. The pin is then inserted into a long, light-weight nylon female connector. The connector thus formed is relatively static resistent and splash-proof. However, the process for forming the connector is somewhat complicated and requires a special crimping tool. It is believed that the present invention overcomes some of the problems inherent in such a prior art system.

SUMMARY OF THE INVENTION

Briefly described, the invention comprises a method and apparatus for forming an electrically insulating, splash-proof connector from the shank of a Keith-type straight needle. The shank of the straight needle is inserted into the connector body through a small aperture. The lead extends into an interior cavity inside of the connector body which shields the lead from the environment. A small rubber grommet at the closed end of the connector body protects the lead from moisture. The lead is secured in the connector body by a locking cap. A pair of resilient, opposed arms are connected to the cap and carry respectively a pair of locking tabs at the ends thereof. The locking tabs mate with corresponding indents in the sides of the connector body. Each tab includes a beveled leading face so that the arms are cammed away from the body during assembly. The cap is locked into position by forcing it over the closed ends of the connector body until the tabs snap into their mating indents.

It is difficult to accidentally remove the locking cap once it is mated with the connector body. This is due to two factors. Firstly, when the cap is locked in position it presents no surface upon which a purchase can be obtained to remove the locking cap. The only way the locking cap can be removed is by the deliberate efforts of the instrument operator or the patient. In other words the exterior geometry of the assembled device makes it very difficult to separate the locking cap from the connector body. Secondly, the structure of the locking tabs is such that it is difficult to force the tabs to back out of the mating indents. The rear surface of the locking tabs presents a relatively vertical face to the locking cavity as opposed to the leading surface of the tabs which presents a bevelled face. Once assembled the lead may be protected by placing a small rubber plug in the open end of the connector body to keep it free of contaminants.

These and other features of the invention will be more fully appreciated by referring to the following drawings.

BRIEF DESCRIPTION OF THE DRAWINGS

FIG. 2a is an end view of the closed end of the connector body according to the preferred embodiment of the invention.

FIG. 2b is a cross-sectional longitudinal view of the connector body illustrated in FIG. 2a.

FIG. 2c is a detail exterior view of the connector body illustrated in FIG. 2b showing the structure and location of the locking indents and arm receiving flat surfaces of the connector body.

FIG. 3b is an end view of the locking end cap illustrated in FIG. 3a.

FIG. 3c is a cross-sectional longitudinal view of the locking end cap illustrated in FIG. 3a.

DETAILED DESCRIPTION OF THE PREFERRED EMBODIMENT

During the course of this description like numbers are used to identify like elements as those elements appear in the different figures that illustrate the invention.

Figure 1:
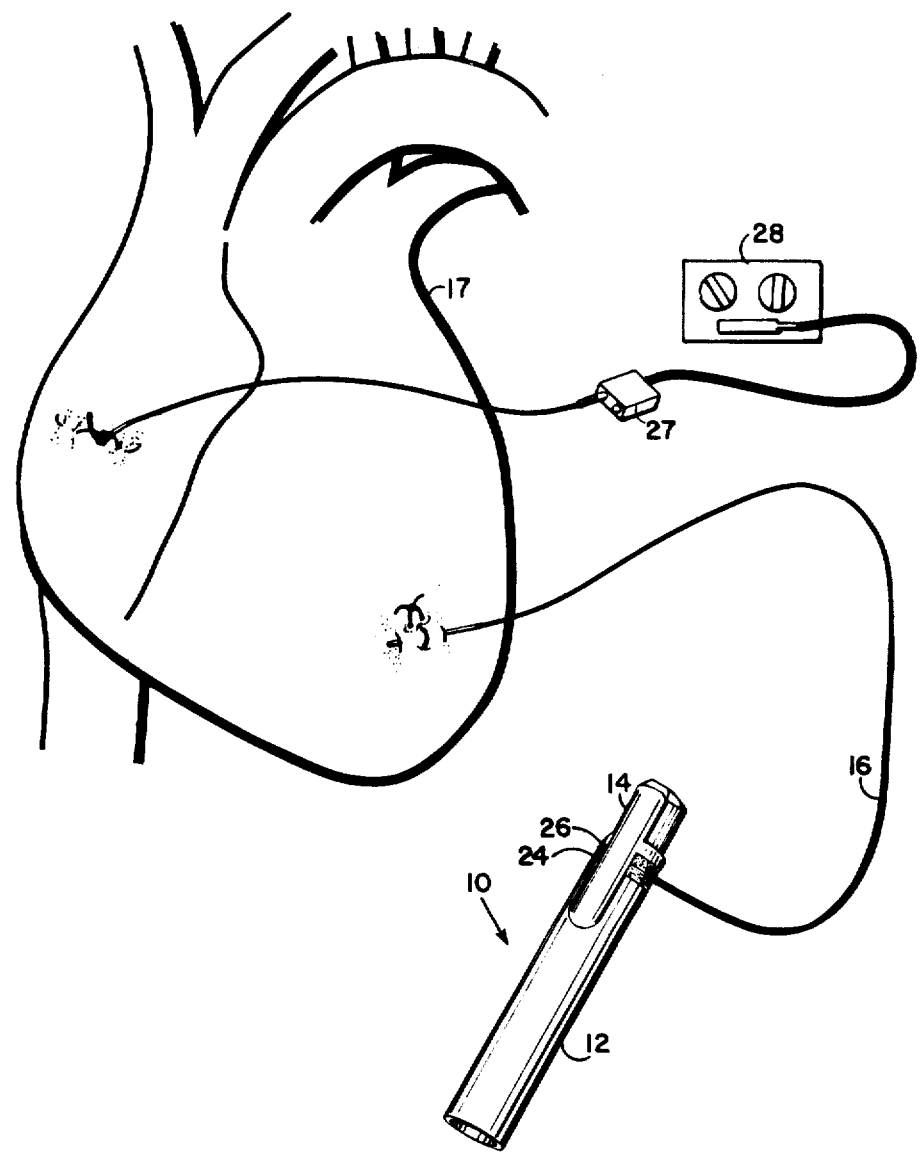
FIG. 1 is a perspective view of the preferred embodiment of the invention as assembled and attached to a heart.
Figure 3B:
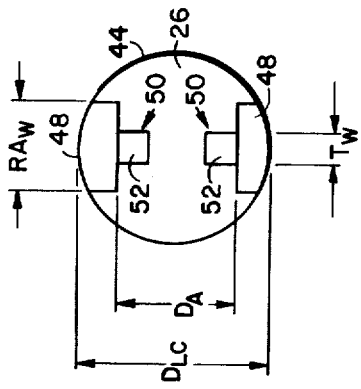
Figure 3A:
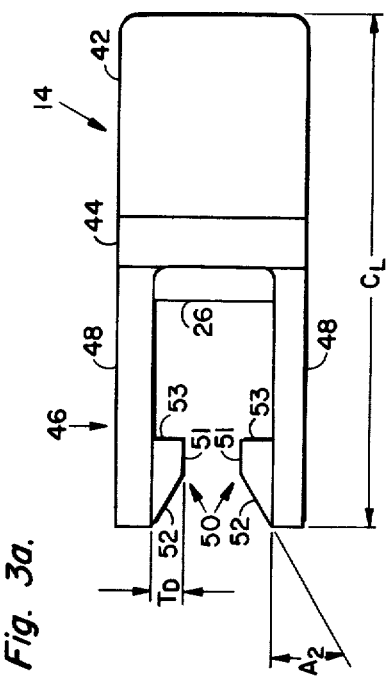
FIG. 3a is a side view of the preferred embodiment of the locking end cap.
Figure 3C:
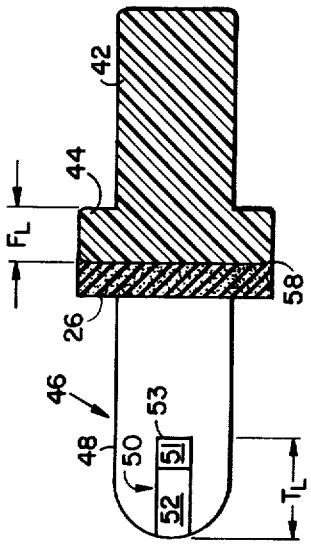
Figure 4:
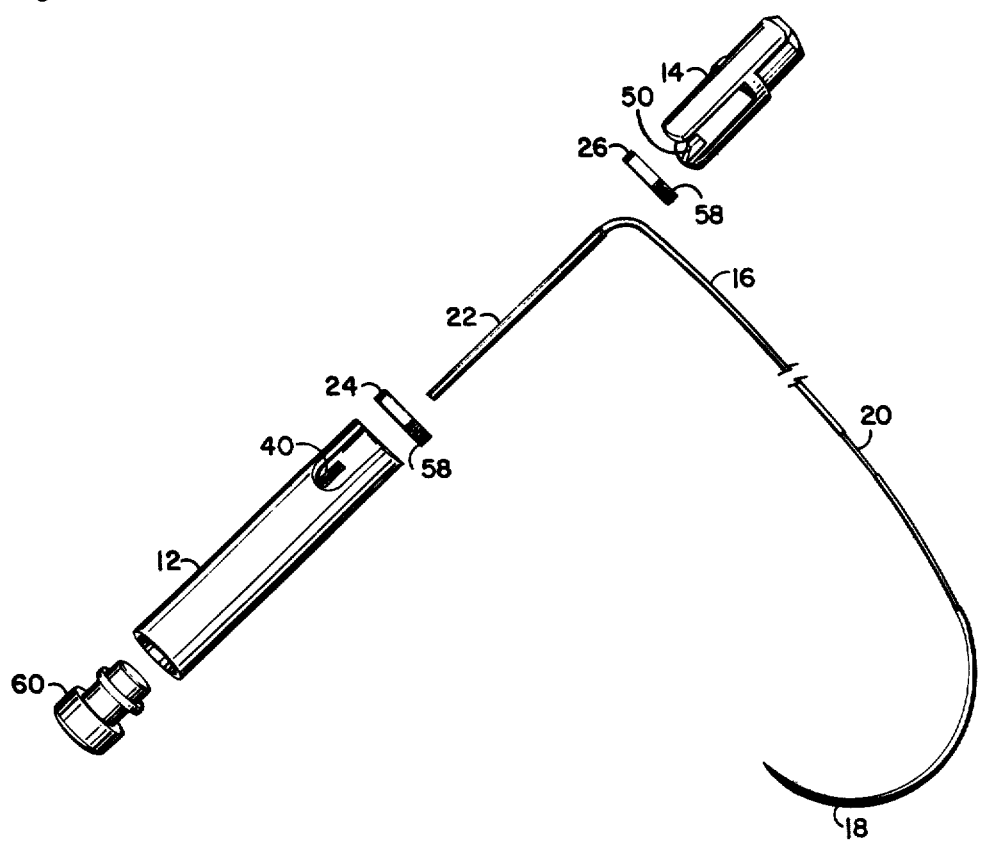
FIG. 4 is an exploded view of the connector assembly illustrated in FIG. 1.

FIG. 1 is a perspective view of the invention 10 showing the connector assembly attached to a cardiac pacing wire 16. The connector assembly 10 includes a connector body 12 and its associated locking cap 14. The other end of wire 16 is normally connected to a circular taper point needle 18 as shown in FIG. 4. A bare spot 20 is typically located on wire 16 a few inches before needle 18. The purpose of bare spot 20 is to make contact with the heart muscle tissue 17. The method of implanting leads in the heart is known to those of ordinary skill in the art and therefore will not be described in further detail. The detailed structure of the connector body 12 is illustrated in FIGS. 2a–2c. Similarly, the detailed structure of the locking cap 14 is illustrated in detail in FIGS. 3a–3c.

The connector body 12 carries a rigid lead 22 which serves as the male portion of the electrical contact of the connector assembly 10. Lead 22 is illustrated in the exploded view of FIG. 4. A resilient grommet 24 attached to connector body 12 is used to keep moisture out of the device. Similarly a resilient pad 26 located in locking cap 14 contacts grommet 24 to further improve the seal. Grommet 24 and pad 26 also further serve to secure lead 22 and wire 16 in the connector assembly 10. A small amount of glue 68 or similar adhesive may be used to keep grommet 24 and pad 26 in place. Lead 22 is formed by cutting or breaking the shaft of a Keith-type straight needle 54 as described in further detail in FIG. 5a. The connector 10 mates with a female connector 27 of a suitable medical instrument 28. Instrument 28 might be a cardiac pacemaker or a heart monitor or other similar device. A plug 60 is received in the open end of the connector body 12 after the invention 10 is assembled so as to protect the interior lead 22 from moisture or other contamination.

The structure of the connector body is illustrated in greater detail in FIGS. 2a–2c. Connector body 12 has a generally cylindrical shape. One end 34 is closed and the other end 30 is open. An interior cavity 32 extends inwardly from opened end 30. Similarly, a much smaller aperture 36 extends from the exterior of the closed end 34 through the connector body 12 and into interior cavity 32. The diameter of aperture 36 is approximately 0.001"–0.004" larger than the diameter of the Keith needle shank. A pair of opposing flat areas 38 extend a distance $F_{FL}$ from the closed end 34 along the length of the body 12. A pair of locking indents 40 are located in flat areas 38 on opposite sides of the connector body 12. Each locking indent 40 includes a sloping front face 39 angled at an angle $A_1$ of approximately 30° and a substantially vertical rear face 41. Aperture 36 is shown as being slightly stepped in FIG. 2b. The small step increase in diameter of aperture 36 is provided to accomodate the swaged increase in diameter where the lead 22 is connected to wire 16.

Locking end cap 14 essentially comprises a relatively flat head portion 42, a circular middle flange portion 44 and a pair of opposed resilient arms 48 each of which carry respectively an inwardly facing locking tab 50. Resilient arms 48 and the associated tabs 50 together comprise a bifurcated spring action locking means 46 which locks the cap 14 onto the end of the connector body 12. Each of the two tabs 50 include a flat inner surface 51, a beveled leading edge surface 52 and a substantially flat vertical rear surface 53. The geometry of each locking tab 50 roughly compliments the geometry of the locking tab receiving indents 40 on the connector body 12. A piece of sponge-like gasket material 26 is attached to the inward face of flange 44 by means of an appropriate adhesive material. Similarly, a piece of resilient gasket material 24 is attached to the closed end 34 of the connector body 12 as previously described. According to the preferred embodiment of the invention gasket material 24 is adhesively attached to the closed end 34 and may include a small hole approximately 1/16" in diameter to guide the insertion of lead 22 into connector body 12.

Figure 5A:
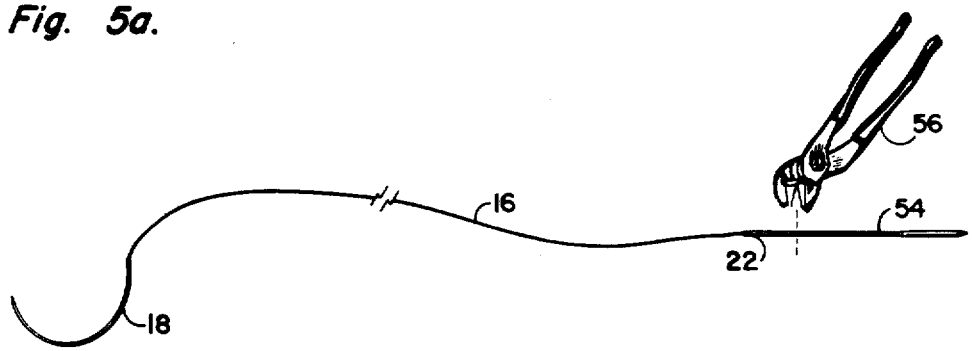
FIGS. 5a through 5c illustrate the steps necessary to assemble the connector according to the preferred embodiment of the invention.
Figure 5B:
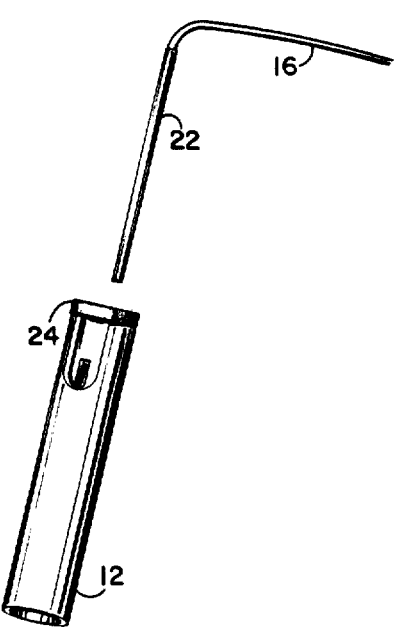
Figure 5C:
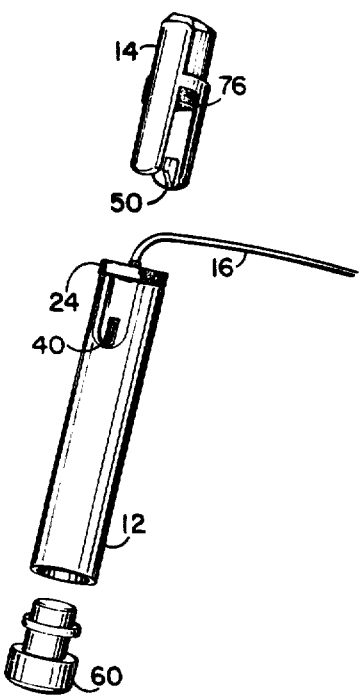

FIGS. 5a–5c illustrate the method by which the invention 10 is assembled. Initially the straight needle 54 is cut with a pair of conventional diagonal pliers 56 so as to create a lead 22 of an appropriate length. That step is illustrated in FIG. 5a. The head of the straight needle is then discarded. Next, the lead 22 is inserted into aperture 36 as far as it will go. The swaged portion of the wire/lead connection will limit the depth of travel of lead 22 into aperture 36. A pilot opening is preferably preformed in resilient pad 24 to guide the insertion of lead 22 into connector body 12. The remaining wire 16 is then bent at right angles so as to clear the connector body 12 and locking cap 14. The intermediate steps are illustrated in FIG. 5b. Finally, as shown in FIG. 5c, the cap 14 is locked into position on the body 12. This is accomplished by forcing the tabs 50 up against the closed end 34 and aligning them with the flat surfaces 38. Pressure will cause the beveled leading face 52 to cam the resilient arms 48 outwardly. Continued pressure will cause the tabs 50 to ride over the flat surface 38 and travel down the connector body 12 until they pop into tab receiving indents 40. Once tabs 50 are engaged in indents 40 they become very difficult to dislodge accidentally.

The device just described is preferably made from ABS plastic. Alternatively other plastics such as nylon or styrene may be acceptable too.

According to the preferred embodiment the connector body 12 and the cap 14 have the following dimensional characteristics:

| Dimension | Size |
|---|---|
| $B_L$ | 0.900" |
| $A_1$ | 30° |
| $D_{CB}$ | 0.250" |
| $D_{IC}$ | 0.204" |
| $F_{FL}$ | 0.300" |
| $D_{FS}$ | 0.050" |
| $D_{FC}$ | 0.075" ± 0.002" |
| $F_W$ | 0.154" ± 0.002" |
| $I_W$ | 0.062" |
| $D_{IE}$ | 0.170" ± 0.001" |
| $F_L$ | 0.060" |
| $T_L$ | 0.125" |
| $C_L$ | 0.660" |
| $T_D$ | 0.040" |
| $A_2$ | 25° |
| $RA_W$ | 0.151" ± 0.001" |
| $D_A$ | 0.155" ± 0.002" |
| $T_W$ | 0.050" |
| $DL_C$ | 0.250" |

As previously described the connector 10 mates with a female lead connected to a medical instrument 28. The instrument 28 is typically a pacemaker or similar therapeutic device. Alternatively, the connector 10 can be attached to a diagnostic device such as an electrocardiogram analyzer machine (EKG). The invention just described has a variety of important advantages over prior art connectors and method for making the same. First of all, it provides an effective means for electrically isolating the terminal end of an electrode when the electrode is not in use. Simultaneously it protects the electrode from other environmental hazards such as liquids and dirt. It is very important to protect the electrode from static electricity since very small spurious electrical charges can cause serious heart fillabrations or arrhythmia. Second, since the electrode is kept clean and is securely attached to the connector body, it forms a superior electrical contact for the therapeutic or diagnostic instrument to which it is ultimately connected. Third, the connector is assembled easily and quickly and does not require any of the special devices, such as crimping tools, which are associated with prior art connectors. Fourth, it is virtually impossible to separate the locking cap from the connector body after the cap has been secured in position. Therefore, an instrument attendant cannot accidentally separate the electrode from the connector. More importantly, a patient can't accidentally expose the electrode to liquids or other environmental hazards. It is possible to manually remove the locking cap, but it takes a great deal of effort. Removal is accomplished by first prying one tab away from the locking hole and then removing the other tab while keeping the first tab away from the connector body. Therefore, removal of the locking cap from the connector body can only be accomplished by very deliberate efforts to do so. Moreover, when the electrode connector is held by the cap such as when the connector is connected to an instrument that manual pressure tends to further secure the lock on the connector body rather than to dislodge the cap. In other words, manipulation of the assembly tends to make the cap lock even tighter. Lastly, the structure of the connector is such that it can be easily manufactured for significantly less cost than is presently associated with electrode connectors.

While the invention has been described with reference to a preferred embodiment thereof it will be appreciated by those of ordinary skill in the art that various changes and modifications can be made to the apparatus and method of the present invention without departing from the spirit and scope thereof. For example, while the device has been described in the context of a temporary cardiac pacing wire electrode it will be appreciated by those of ordinary skill in the art that the invention could be employed for other biological connections as well.

I claim:

1. An electrical connector apparatus for connecting a rigid male electrical lead with a flexible wire attached thereto to medical electronic instruments, said apparatus comprising:
    a non-conductive connector body having a closed end and an open end having an interior cavity therein, said closed end having an aperture therethrough extending from the outside of said connector body into said interior cavity, said aperture being of sufficient size to receive said rigid male electrical lead therein, said non-conductive connector body including indent means thereon;
    a cap means receivable on said closed end of said connector body for holding said rigid male electrical lead in said aperture and for securing said flexible wire lead to said rigid male electrical lead in an orientation that is substantially perpendicular to said rigid male electrical lead; and,
    cap locking means for locking said cap means to said connector body, said cap locking means comprising a bifurcated spring-action means including:
        at least two resilient arm means attached to said cap means at one end; and,
        tab means attached to said resilient arm means and oriented to be received in said indent means in said connector body,
    wherein said cap means positively locks said rigid male electrical lead in said non-conductive connector body.

2. The apparatus of claim 1 wherein said tab means comprise:
    at least two tabs respectively attached to the ends of said at least two arms means furtherest removed from said cap means.

3. The apparatus of claim 2 wherein said tabs face inwardly and have a beveled front leading surface so that they can ride up over the connector body during assembly.

4. The apparatus of claim 3 wherein said connector body includes at least two surfaces thereon for receiving the arms of said cap locking means, so that the exterior surface of said connector when assembled is substantially unchanged in geometry from the connector body to the cap means.

5. The apparatus of claim 4 further including:
    resilient gasket means attachable to said closed end of said connector body for securing and sealing said lead with respect to said connector apparatus,
    wherein said lead passes through the body of said resilient gasket means during assembly.

6. The apparatus of claim 5 further comprising:
    a resilient pad means attachable to said cap means for further securing said lead when said cap is locked in position on said connector body.

7. The apparatus of claim 6 wherein said cap means further includes:
    a flange portion connected to said arm means; and,
    a substantially flat top portion attached to said flange portion on the side thereof opposite from said arm means.

8. The apparatus of claim 7 wherein said connector is formed from plastic-like materials having antistatic properties.

9. The apparatus of claim 8 further comprising:
    removable resilient plug means receivable in the open end of said connector body for selectively sealing off said interior cavity and said lead from the exterior environment.

10. A method for attaching a rigid male electrical lead having a flexible wire attached thereto to a non-conductive connector for use with medical electronic instruments, said method comprising the steps of:
    inserting said rigid male electrical lead into a non-conductive body, said non-conductive body having a closed end and an open end having an interior cavity therein, said closed end having an aperture therethrough for receiving said rigid male electrical lead so that said rigid male electrical lead extends into said interior cavity, said connector body having at least two locking indents therein;
    pressing a locking cap having at least two resiliently mounted locking tabs thereon over the closed end of said connector body so that said tabs are biased into said indents thereby locking said locking cap to said body and bending said flexible wire to an angle that is oriented substantially 90° with respect to said rigid male electrical lead,
    whereby said locking cap positively prevents said rigid male lead from backing out of said non-conductive connector body.

* * * * *